United States Patent [19]

Kinsman

[11] Patent Number: 5,631,215
[45] Date of Patent: May 20, 1997

[54] PROCESS FOR MAKING HIGH MOISTURE CONTENT SOAP BARS

[75] Inventor: Donald V. Kinsman, Ft. Thomas, Ky.

[73] Assignee: Henkel Corporation, Plymouth Meeting, Pa.

[21] Appl. No.: 310,907

[22] Filed: Sep. 22, 1994

Related U.S. Application Data

[63] Continuation-in-part of Ser. No. 278,464, Jul. 21, 1994, abandoned.

[51] Int. Cl.$^6$ .................... C11D 9/00; C11D 15/04; C11D 13/00
[52] U.S. Cl. .................... 510/130; 510/141; 510/146; 510/151; 510/152; 510/447; 510/470; 510/481; 510/488; 510/491
[58] Field of Search .................... 252/108, 121, 252/174.17, 174.18, DIG. 5, DIG. 16, 367, 368; 510/130, 141, 146, 151, 152, 447, 470, 481, 488, 491

[56] References Cited

U.S. PATENT DOCUMENTS

| | | | |
|---|---|---|---|
| 2,649,417 | 8/1953 | Compa | 252/109 |
| 2,970,116 | 1/1961 | Kelly et al. | 252/368 |
| 3,274,119 | 9/1966 | Goldwasser et al. | 252/368 |
| 3,576,749 | 4/1971 | Megson et al. | 252/132 |
| 4,493,786 | 1/1985 | Joshi | 252/368 |
| 4,565,647 | 1/1986 | Llenado | 252/354 |
| 4,574,053 | 3/1986 | Kinsman et al. | 252/131 |
| 4,861,507 | 8/1989 | Gervasio | 252/108 |
| 4,963,284 | 10/1990 | Novakovic et al. | 252/108 |
| 5,043,091 | 8/1991 | Joshi et al. | 252/174.17 |
| 5,194,172 | 3/1993 | Taneri et al. | 252/130 |
| 5,204,014 | 4/1993 | Redd et al. | 252/DIG. 5 |
| 5,219,487 | 6/1993 | Heile, Jr. et al. | 252/108 |
| 5,225,097 | 7/1993 | Kacher et al. | 252/112 |
| 5,225,098 | 7/1993 | Kacher et al. | 252/112 |
| 5,227,086 | 7/1993 | Kacher et al. | 252/112 |
| 5,264,144 | 11/1993 | Moroney et al. | 252/117 |
| 5,264,145 | 11/1993 | French et al. | 252/117 |
| 5,266,690 | 11/1993 | McCurry, Jr. et al. | 536/18.6 |
| 5,294,363 | 3/1994 | Schwartz et al. | 252/108 |
| 5,296,159 | 3/1994 | Wilson et al. | 252/DIG. 5 |
| 5,300,242 | 4/1994 | Nichols et al. | 252/38 |
| 5,300,249 | 4/1994 | Schwartz et al. | 252/DIG. 5 |

FOREIGN PATENT DOCUMENTS

| | | | |
|---|---|---|---|
| 0463912 | 1/1992 | European Pat. Off. | C11D 9/26 |
| 0548204 | 6/1993 | European Pat. Off. | C11D 9/26 |
| WO9205241 | 4/1992 | WIPO | C11D 9/26 |

*Primary Examiner*—Glenn A. Caldarola
*Assistant Examiner*—Patricia L. Hailey
*Attorney, Agent, or Firm*—Wayne C. Jaeschke; John E. Drach; Henry E. Millson, Jr.

[57] ABSTRACT

Personal cleansing bars having a relatively high moisture content are made by forming a soap composition comprised of a neutralized tallow-free fatty acid mixture having an iodine value of less than about 7 and an alkyl polyglycoside of the formula I $$R_1O(Z)_a \quad I$$

wherein $R_1$ is a monovalent organic radical having from about 6 to about 30 carbon atoms; Z is saccharide residue having 5 or 6 carbon atoms; a is a number having a value from 1 to about 6. The soap composition is then finished to produce a bar having from about 15% to about 30% by weight of water.

40 Claims, No Drawings

PROCESS FOR MAKING HIGH MOISTURE CONTENT SOAP BARS

CROSS-REFERENCE TO RELATED APPLICATIONS

This application is a continuation-in-part of Application Ser. No. 08/278,464, filed on Jul. 21, 1994, now abandoned the entire contents of which are incorporated herein by reference.

BACKGROUND OF THE INVENTION

1. Field of the Invention

This invention relates to a process for making high moisture content soap bars.

2. Description of the Related Art

Soap in bar form has long been in use for cleansing purposes. Those skilled in the art use the term soap to designate the reaction product of a carboxylic acid with a base, typically a metal hydroxide or carbonate. The resulting salt has both a polar hydrophilic end and a non-polar lipophilic end which facilitates the removal of oils and other non-polar materials from the skin or other surface in the presence of water.

Bar soaps are customarily prepared either by framing/ casting or by refining/plodding. Framed or cast soaps are prepared by reacting an appropriate fat, oil or carboxylic acid with a base in the presence of water to form soap, pouring the molten soap containing about 30% water into a frame or a mold, allowing the soap to cool and harden, and removing the soap having about 20% to 25% water by weight in a bar form. Those skilled in the soap-making art are aware that the carboxylic acid hereafter referred to as a fatty acid is readily available as an article of commerce. The fatty acid also can be obtained from a fat, such as tallow or lard, from an oil, such as coconut oil, palm oil, palm kernel oil, or olive oil, or from combinations of fats and oils. Fats and oils are comprised in substantial part of glycerides of varying chain lengths, which are esters of glycerol (glycerine) and fatty acids. Under alkaline conditions, and in the presence of heat, the glycerides constituting the fats and oils break down to form fatty acid salts, also known as soaps, and glycerine.

Refined/plodded soap bars are produced by subjecting the neutralized soap to various finishing steps which alter the crystalline matrix of the soap from the omega phase, as formed in framed/cast soap bars, to the beta phase. A more detailed discussion may be found in Bailey's Industrial Oil And Fat Products, 4th ed., Vol. 1, p. 558 et seq. (1979). Prior to conversion the soap is first dried from a moisture level of approximately 30% to a level in the range of about 10% to about 14%. Next, the dried soap is generally sent to a simple paddle-type mixer where a variety of additives can be introduced. From this mixer the soap is then sent either directly to a refiner or optionally to a three-roll mill and then to the refiner. Both the refiner and the mill subject the soap to compression and an intense shearing action which tend to orient the soap crystals and convert the soap largely to the beta-phase. After refining, the soap is compressed into a dense, coherent form in a plodding operation which forms solid portions which are suitable for stamping into bars.

The drying step is necessary to remove the "gummy" texture and excessive pliability of the soap mass which exist typically at higher moisture levels. In the production of plodded bars, drying to from about 10% to about 14% moisture is necessary to permit the soap mass to be processed through the finishing equipment. Drying on a commercial basis is achieved by several different methods. One procedure employs a water-chilled roll in combination with a second feed roll to spread molten, neutralized soap into a thin, uniform layer. The cooled soap is then scraped from the roll to form chips and dried to a specific moisture level in a tunnel dryer. Soap chips already having a low moisture level (about 10% to 11%) are further dried by repeatedly conducting the chips through close-set water cooled steel rolls (i.e., three-roll mill) in the procedure known as milling described above. A relatively modern technique for the drying of soap is known as spray drying. This process directs molten soap to the top of a tower via spray nozzles. The sprayed soap hardens and then dries in the presence of a current of heated air. Vacuum may be applied to facilitate the removal of water. Though typically the moisture level of plodded soap bars is maintained in the range of about 10% to about 14%, a plodded soap bar containing greater than 14% moisture is known in the prior art.

The incorporation of an alkyl polyglycoside permits the moisture level of the soap bars to be maintained at relatively high levels thereby reducing manufacturing costs by reducing the drying times and drying energy requirements. The presence of an alkyl polyglycoside in a soap produces a bar which exhibits increased flash foaming and a richer and creamier lather. Prior to the present invention, direct incorporation of an alkyl polyglycoside into standard soap making operations which employ tallow/coco soaps made further refining difficult if not impossible. On refining, tallow/ coco soaps containing alkyl polyglycosides were found to be too sticky and unsuitable for plodding and stamping.

SUMMARY OF THE INVENTION

It is an object of the present invention to produce a personal cleansing bar having a relatively high moisture content. It is also an object of the present invention to produce a personal cleansing bar having a relatively high moisture content and which is mild to the skin, lathers easily, prevents scum formation, is biodegradable and exhibits increased flash foaming and a richer and creamier lather.

The present invention relates to a process for making a personal cleansing bar which has a relatively high moisture content. The term tallow-free fatty acid as used herein is defined as one or more fatty acids which is free of tallow fatty acids and has an iodine value of less than about 7. Tallow-free fatty acids include such as fatty acids as palmitic acids, stearic acids, coco acids, and palm kernel acids as described below.

The first step of the process according to the invention comprises forming a neutralized fatty acid composition which is comprised of a neutralized tallow-free fatty acid mixture and a nonionic surfactant which is an alkyl polyglycoside of the formula I $$R_1 O(Z)_a \qquad\qquad\qquad I$$

wherein $R_1$ is a monovalent organic radical having from about 6 to about 30 carbon atoms; Z is saccharide residue having 5 or 6 carbon atoms; a is a number having a value from 1 to about 6. The tallow-free fatty acid mixture has an iodine value of less than about 7. The second step in the process according to the invention is the finishing step which comprises further processing the neutralized fatty acid-alkyl polyglycoside composition to produce a bar having from about 15% to about 30% by weight of water.

A variation of the process according to the invention permits the use of an alkyl polyglycoside in a standard soap manufacturing process wherein tallow fatty acid soaps are incorporated. This is accomplished by mixing the neutralized fatty acid composition containing an alkyl polyglycoside and neutralized tallow-free fatty acids to form a soap composition having a moisture content of from about 15% to about 30% with a standard neutralized tallow/coco fatty acid mixture having a moisture content of less than about 15% by weight prior to the standard milling-refining-plodding operations, preferably at the beginning of the finishing operation. The neutralized fatty acid composition containing an alkyl polyglycoside is separately prepared and the standard neutralized tallow/coco fatty acid mixture is dried to a moisture content of less than about 15% by weight before the two are mixed together. This variation in the process according to the invention permits the production of relatively high moisture content soap bars using standard soap bar production facilities. Since no special equipment is required, the cost of producing relatively high moisture content soap bars is comparable to the cost of making conventional tallow/coco soap bars.

The process according to the invention produces a personal cleansing bar having a relatively high moisture content and which is mild to the skin, lathers easily, prevents scum formation, is biodegradable and exhibits increased flash foaming and a richer and creamier lather.

DESCRIPTION OF THE PREFERRED EMBODIMENTS

Other than in the claims and in the operating examples, or where otherwise indicated, all numbers expressing quantities of ingredients or reaction conditions used herein are to be understood as modified in all instances by the term "about".

In carrying out the process according to the invention, bars containing the neutralized tallow-free fatty acid mixture-alkyl polyglycoside soap composition may be formed in either of two ways. The first of such methods can be accomplished by mixing appropriate amounts of a tallow-free fatty acid mixture having an iodine value of less than about 7 and an alkyl polyglycoside surfactant of formula I and then neutralizing the mixture with any neutralizing agent known to those skilled in the art. Such neutralizing agents include, but are not limited to, alkali metal hydroxides and carbonates, such as sodium hydroxide, potassium hydroxide, sodium carbonate, potassium carbonate and mixtures thereof. The second method can be accomplished by first neutralizing a tallow-free fatty acid mixture having an iodine value of less than about 7 with any neutralizing agent known to those skilled in the art such as those disclosed above and then adding the alkyl polyglycoside surfactant.

The tallow-free fatty acid mixture suitable for use in the process according to the invention will typically be composed of two fatty acid components. The first component can be either coco fatty acid or palm kernel fatty acid. A typical coco fatty acid is composed primarily of from 45% to 55% by weight lauric acid, from 15% to 23% by weight of myristic acid, from 8% to 11% of palmitic acid, from 1% to 10% by weight of stearic acid, from 1% to 14% of caprylic and captic acids, and from 1% to 8% by weight of oleic acid. A typical palm kernel fatty acid is composed primarily of from 40% to 52% by weight lauric acid, from 14% to 18% by weight of myristic acid, from 7% to 9% of palmitic acid, from 1% to 3% by weight of stearic acid, from 3% to 5% of caprylic acid, from 3% to 7% of capric acids, from 11% to 19% by weight of oleic acid, and from 0.5% to 2% by weight of linoleic acid.

Preferably, the first fatty acid component will contain from 48% to 51% by weight lauric acid, from 18% to 20% by weight of myristic acid, from 9% to 10% of palmitic acid, from 6% to 8% by weight of stearic acid, from 1% to 3% by weight of oleic acid, and from 12% to 13% by weight of caprylic and capric acids.

The second fatty acid component will be stearic-palmitic acid combinations commercially available as "stearic acid" or "palmitic acid" and which are comprised of stearic acid and palmitic acid.

One preferred second fatty acid component, contains from 45% to 65% by weight stearic acid and from 25% to 55% by weight of palmitic acid. Another preferred second fatty acid component contains from 1% to 40% by weight stearic acid and from 58% to at least about 99% by weight of palmitic acid.

The process according to the invention may be carried out in an alternate manner which permits the use of an alkyl polyglycoside in a standard soap manufacturing process wherein tallow fatty acid soaps are included in preparing the bars. This is accomplished by mixing the neutralized fatty acid composition containing an alkyl polyglycoside and neutralized tallow-free fatty acids having a moisture content of from about 15% to about 30% with a separately prepared neutralized tallow/coco fatty acid mixture which has been dried to about 12% moisture content. The mixing will take place prior to the standard milling-refining-plodding operations, preferably at the beginning of the finishing operation. The tallow/coco fatty acid mixture can contain from about 80% tallow fatty acids and 20% coco fatty acids to about 20% tallow fatty acids and 80% coco fatty acids, with preferred ratios ranging from about 80% tallow fatty acids and 20% coco fatty acids to about 50% tallow fatty acids and 50% coco fatty acids. The composition of a typical coco fatty acid has been described above.

A tallow fatty acid is one which contains from about 45% to about 55% by weight of a mixture of saturated fatty acids a majority of which are stearic and palmitic acids and from about 45% to about 55% by weight of a mixture of unsaturated fatty acids a large majority of which is oleic acid and which may also contain linoleic acid and linolenic acid. As desired, the linolenic and linoleic acids may also be eliminated by hydrogenation. An example of a typical commercially available unhydrogenated tallow fatty acid is EMERY® 531 Tallow Fatty Acid, a trademark product of Henkel Corporation, Emery Group, Cincinnati, Ohio. The typical specifications for EMERY® 531 Tallow Fatty Acid are: titer 36°–44° C., maximum iodine value of 45–70, acid value of 200–208, color value of 19/81 (% trans. 440/550 (nm., min.). The typical composition of EMERY® 531 Tallow Fatty Acid is: 2.5% myristic acid, 0.5% pentadecanoic acid, 27% palmitic acid, 1% margaric acid, 17% stearic acid, 4% palmitoleic acid, 42 oleic acid, 5% linoleic acid, 1% linolenic acid. In this alternate method of carrying out the process according to the invention, two soap bases are blended together prior to or during the finishing step. The first of these soap bases is comprised of a soap composition which is comprised of a neutralized tallow-free fatty acid mixture and a nonionic surfactant which is an alkyl polyglycoside of the formula I as set forth above and which is comprised of about 20% to 30% by weight moisture. The second of the two soap bases is comprised of a neutralized fatty acid mixture comprised of a tallow/coco fatty acid mixture and contains about 12% by weight moisture.

In the variation of the process according to the invention in which a neutralized tallow-free fatty acid-alkyl polyglycoside mixture is mixed with a standard neutralized tallow/coco fatty acid mixture, the mixing can take place at any convenient point in the bar soap production process after the tallow/coco fatty acid mixture has been neutralized and dried to a typical refining moisture levels of less than about 15%, preferably from about 10% to about 14%. The preferred mixing point is at the start of the finishing portion of the operation. In the preferred case, the neutralized tallow-free mixture containing the alkyl polyglycoside and the typical tallow/coco base stock are blended in an amalgamator along with any other desired additives such as perfume, colorant, bacteriostat, preservatives, or superfatting agents and the mix is then sent through the standard milling-refining-plodding process.

In a preferred embodiment, the neutralzied tallow-free fatty acid-alkyl polyglycoside soap base having a moisture content of from about 15% to about 30% is refined to form pellets. The refined pellets are then mixed in an amalgamator with a stock comprised of a standard tallow/coco soap base and dried to a moisture level of about 12% by weight to form a combined soap base. The combined soap base is then refined and plodded. It is essential that the neutralzied tallow-free fatty acid-alkyl polyglycoside soap base be refined at 15% –30% moisture and that the standard tallow/coco soap base is dried to a moisture level of less than about 15% by weight before mixing with the neutralzied tallow-free fatty acid-alkyl polyglycoside soap base. In another preferred embodiment, the neutralzied tallow-free fatty acid-alkyl polyglycoside soap base is refined by pelletizing and then blended directly with a dried standard tallow/coco soap base in the refiner after the amalgamator stage.

Once the neutralzied tallow-free fatty acid-alkyl polyglycoside soap mixture is formed according to either method of carrying out the process according to the invention, it can then be transferred immediately to the finishing equipment without further drying, though typically some slight amount of moisture loss will occur, if merely by ambient air drying. The finishing equipment typically consists of a combination of a refiner and plodder, units which are well known in the art. The refiner, plodder, and an integrated refiner-plodder are manufactured by companies such as Mazzoni, s. P. A., and are used to remove hard particles from the soap mass and subject the soap to high shear and compression. This working action tends both to orient the crystalline fibers of the soap in a uniform direction and to convert the soap from the omega-phase as principally found in framed soaps to the beta-phase. The typical refiner consists basically of an inlet hopper to receive the neutralized soap, a series of increasingly fine screens located in a cylindrical barrel, and one or more motor-driven spiral compression screws which force the soap through the screens under high pressure to remove particulate contaminants and alter the phase of the soap. The typical plodder forces the filtered soap through a temperature-controlled compression cylinder and then through a diameter orifice at temperature-controlled reduced high pressure. The soap as it exits the orifice is in the shape of a continuous log in a dense, coherent form and is suitable for cutting and stamping to form soap bars. The process of this invention contemplates that the water content of the plodded bar is about 15% to about 30% by weight. In contrast, typical tallow/coco bars will have about 8% to about 12% water content. The higher water content of the bars produced according to the teachings of this invention has no adverse effect on the bars' firmness or lathering properties. Subsequent reduction of the moisture level of the finished bars to about 5%, as would occur on extended storage, has no adverse effect on the performance of the bars. Further, because the fatty acid blend is either totally free of tallow fatty acids as compared to typical tallow/coco bars and thus has fewer reactive double bond sites, or has a reduced amount of such tallow/coco fatty acids, the formation of color bodies and odor-causing species is minimized; as a result, the initial and long-term color and odor of the bars prepared from the blend are noticeably improved.

The alkyl polyglycosides which can be used in the process according to the invention have the formula I $$R_1O(Z)_a \qquad \qquad I$$

wherein $R_1$ is a monovalent organic radical having from about 6 to about 30 carbon atoms; Z is saccharide residue having 5 or 6 carbon atoms; a is a number having a value from 1 to about 6. The alkyl polyglycosides which can be used in the compositions according to the invention have the formula I and are commercially available, for example, as APG®, GLUCOPON®, or PLANTAREN® surfactants from Henkel Corporation, Ambler, Pa., 19002. Examples of such surfactants include but are not limited to:

1. APG® 225 Surfactant—an alkyl polyglycoside in which the alkyl group contains 8 to 10 carbon atoms and having an average degree of polymerization of 1.7.
2. APG® 425 Surfactant—an alkyl polyglycoside in which the alkyl group contains 8 to 16 carbon atoms and having an average degree of polymerization of 1.6.
3. APG® 625 Surfactant—an alkyl polyglycoside in which the alkyl groups contains 12 to 16 carbon atoms and having an average degree of polymerization of 1.6.
4. APG® 325 Surfactant—an alkyl polyglycoside in which the alkyl groups contains 9 to 11 carbon atoms and having an average degree of polymerization of 1.6.
5. GLUCOPON® 600 Surfactant—an alkyl polyglycoside in which the alkyl groups contains 12 to 16 carbon atoms and having an average degree of polymerization of 1.4.
6. PLANTAREN® 2000 Surfactant—a $C_{8-16}$ alkyl polyglycoside in which the alkyl group contains 8 to 16 carbon atoms and having an average degree of polymerization of 1.4.
7. PLANTAREN® 1300 Surfactant—a $C_{12-16}$ alkyl polyglycoside in which the alkyl groups contains 12 to 16 carbon atoms and having an average degree of polymerization of 1.6.

Other examples include alkyl polyglycoside surfactant compositions which are comprised of mixtures of compounds of formula I wherein Z represents a moiety derived from a reducing saccharide containing 5 or 6 carbon atoms; a is zero; and $R_1$ is an alkyl radical having from 8 to 20 carbon atoms. The compositions are characterized in that they have increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked alkyl polyglycosides, can be prepared by separation of the monoglycoside from the original reaction mixture of alkyl monoglycoside and alkyl polyglycosides after removal of the alcohol. This separation may be carried out by molecular distillation and normally results in the removal of about 70–95% by weight of the alkyl monoglycosides. After removal of the alkyl monoglycosides, the relative distribution of the various components, mono- and poly-glycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in U.S. Pat. No. 5,266,690, the entire contents of which are incorporated herein by reference.

The amount of total fatty acid mixture, either all tallow-free fatty acid or a combination of tallow-free and tallow/coco fatty acids mixtures which can be used in the process according to the invention can range from about 80% to 99% by weight of the starting fatty acid-alkyl polyglycoside mixture. The preferred amount is from about 80% to 95%. The most preferred amount is from about 90% to about 95% by weight of the starting fatty acid-alkyl polyglycoside mixture.

The amount of alkyl polyglycoside which can be used in the process according to the invention can range from about 1% to about 20% by weight of the starting fatty acid alkyl polyglycoside mixture. The preferred amount is from about 5% to about 15%. The most preferred amount is from about 5% to about 10% by weight of the starting fatty acid alkyl polyglycoside mixture.

The weight ratio of the first tallow-free fatty acid to the second tallow-free fatty acid can range from about 80/20 to about 20/80. The preferred weight ratio of the first fatty acid to the second fatty acid is from about 60/40 to about 40/60. The most preferred weight ratio of the first fatty acid to the second fatty acid is 40/60.

In the variation of the process according to the invention which comprises mixing a neutralized tallow-free fatty acid composition containing an alkyl polyglycoside of the formula I to a standard neutralized tallow/coco fatty acid mixture, the weight ratio of the neutralized tallow-free fatty acid-alkyl polyglycoside composition to the tallow/coco fatty acid mixture can be any value and will depend upon the desired properties of the soap bar produced by the process. For most applications, the ratio will typically range from about 80/20 to about 20/80 and preferably from about 60/40 to about 40/60.

While the methods of making soap bars according to the invention contemplate the use of an alkyl polyglycoside as a syndet (synthetic detergent) surfactant component, other syndet surfactants can also be used in combination with an alkyl polyglycoside. Syndet surfactants suitable for use in combination with the alkyl polyglycoside surfactants set forth herein include anionic, nonionic, cationic and amphoteric surfactants and mixtures thereof. Especially useful are those surfactants which are well known to be especially mild properties as regards skin care. Such surfactants include, but are not limited to, alkali metal salts of: alkyl isethionates; e.g. sodium cocoyl—or lauryl isethionate; sarcosinates, sulfosuccinates, taurates and ethoxylated fatty alcohols.

The following examples are meant to illustrate but not limit the invention.

EXAMPLE 1

Soap Bar Formation Method

Approximately 1500 grams of the fatty acid mixture containing 57% by weight of a first fatty acid component and 38% by weight of a second fatty acid component. The first fatty acid component was a stearic-palmitic acid, available commercially as, for example, EMERSOL® 132 Stearic Acid, a trademark product of Henkel Corporation, Emery Group, Cincinnati, Ohio., and which contained (average weight percent) 2.5% myristic acid, 1% pentadecanoic acid, 50% palmitic acid, 1.5% margaric acid, and 45.5% stearic acid. The second fatty acid component was a coco fatty acid, available commercially as, for example, EMERY® 625 Partially Hydrogenated Coconut Fatty Acid, a trademark product of Henkel Corporation, Emery Group, Cincinnati, Ohio., and which contained (average weight percent) 49% lauric acid, 19% myristic acid, 9% palmitic acid, 7% stearic acid, 7% caprylic acid, 6% capric acid, and 3% oleic acid. The mixture was charged to a stainless steel, 4 quart Hobart mixer bowl and melted over a conventional steam table at a temperature of 65°±5° and agitated thoroughly. About 158 grams of an alkyl polyglycoside an alkyl polyglycoside in which the alkyl groups contains 12 to 16 carbon atoms and having an average degree of polymerization of 1.6, commercially available, for example, as GLUCOPON® 625 surfactant, a trademark product of Henkel Corporation, Ambler, Pa, 19002, was added either at this point or after the next (neutralization) step.

An amount of 98% active NaOH equimolar to that of the fatty acid mixture, as calculated from the acid value, was then weighed and dissolved in distilled water. The amount of distilled water plus water from the added alkyl polyglycoside solution was sufficient to produce a neutralized soap having about 30% moisture. Typically, for a 1500 gram charge of fatty acid mixture, about 600 grams of distilled water was used.

The NaOH solution was cooled to about room temperature (30°±5°). When the fatty acid mixture and NaOH solution were within the proper temperature range, the fatty acid mixture was agitated in the Hobart mixer by means of a paddle-type blade. The NaOH solution was added slowly to the fatty acid mixture with continued agitation. After the alkaline solution addition was completed, agitation was continued for several minutes to ensure thorough mixing and complete neutralization. The viscous molten soap was then poured into a glass or plastic pan. While it was possible to process the soap immediately after neutralization, the soap mass was typically allowed to stand for about 1–2 hours to dissipate the heat generated during the neutralization step.

After hardening, the neutralized soap was placed into the hopper of a lab scale Mazzoni 100 Refiner-Plodder which was of conventional design and which approximates the operation of commercial scale equipment. The soap was forced several times each through a series of three increasingly fine screens, passed through a reduced diameter orifice under pressure, and stamped to form a soap bar.

The point of addition of alkyl polyglycoside surfactant in this process as discussed above did not affect the lathering characteristics of the resulting soap bars. The bars made from each of the alkyl polyglycoside surfactant modifications and those made without the use of alkyl polyglycoside surfactant were tested by a panel for flash foaming, lather volume, and lather richness/creaminess on a scale of from 1 (poorest rating) to 5 (very favorable rating). The results of the panel evaluation are given in Table 1 below.

TABLE 1

|  | Flash Foam | Lather Volume | Lather Rich/Cream |
|---|---|---|---|
| With GLUCOPON ® 625 | 3.3 | 3.0 | 2.8 |
| Without GLUCOPON ® 625 | 2.6 | 2.6 | 2.1 |

EXAMPLE 2

Soap bars containing fatty acids different from those used in Example 1 above can be prepared by the same procedure as set forth in Example 1. Table 2 sets forth possible soap bar compositions which should result in soap bars according to the invention.

TABLE 2

| Component[1] | Ex. 2 | Ex. 3 | Ex. 4 | Ex. 5 | Ex. 6 | Ex. 7 | Ex. 8 |
|---|---|---|---|---|---|---|---|
| A | 54 |  | 38 |  | 48 |  |  |
| B |  | 42.5 |  |  |  |  | 57 |
| C |  |  |  | 54 |  | 68 |  |
| D | 36 |  | 57 | 36 |  |  | 38 |
| E |  | 42.5 |  |  |  | 17 |  |
| F | 10 |  |  | 10 | 20 |  |  |
| G |  |  | 5 |  |  | 15 |  |
| H |  | 15 |  |  |  |  | 5 |
| I | 30 | 30 | 30 | 30 | 30 | 30 | 30 |
| J | N | N | N | N | N | N | N |

[1]The amount of each of components A–H is expressed on a 100% solids basis.
A = EMERSOL ® 132 NF Lily ® Stearic Acid which contains 2.5% myristic acid, 1% pentadecanoic acid, 50% palmitic acid, 1.5% margaric acid, and 45.5% stearic acid.
B = EMERY ® 420 Stearic Acid which contains 4% myristic acid, 0.5% pentadecanoic acid, 25% palmitic acid, 1.5% margaric acid, and 65% stearic acid.
C = EMERSOL ® 143 Palmitic Acid which contains a trace of myristic acid, 0.5% pentadecanoic acid, 91% palmitic acid, 4.5% margaric acid, and 4% stearic acid.
D = EMERY ® 625 Partially Hydrogenated Coconut Fatty Acid which contains 19% myristic acid, 9% palmitic acid, 7% stearic acid, 3% oleic acid, 49% lauric acid, 6% capric acid, and 7% caprylic acid.
E = EMERY ® 622 Coconut Fatty Acid which contains 19% myristic acid, 9% palmitic acid, 2% stearic acid, 8% oleic acid, 48% lauric acid, 6% capric acid, and 7% caprylic acid.
F = GLUCOPON ® 625 Surfactant which is a 50% aqueous solution of a C-12 to C-16 alkyl polyglycoside having an average DP of 1.6.
G = GLUCOPON ® 425 Surfactant which is a 50% aqueous solution of a C-8 to C-16 alkyl polyglycoside having an average DP of 1.6.
H = GLUCOPON ® 225 Surfactant which is a 50% aqueous solution of a C-8 to C-10 alkyl polyglycoside having an average DP of 1.7.
I = an amount of water sufficient to produce a soap bar having about 30% moisture.
J = 98% NaOH sufficient to neutralize the fatty acid mixture based on the acid values of the fatty acids and to effect a less than 1% excess caustic level after neutralization.

EXAMPLE 9

A typical 80/20 tallow/coco soap stock made from EMERY® 401 Fatty Acid and EMERY® 625 Partially Hydrogenated Coconut Fatty Acid was dried down to a standard tallow/coco soap processing moisture of about 12% before finishing by air drying.

EXAMPLE 10

A mixture was prepared which contained 2.5% of GLUCOPON® 625 surfactant(100% activity) and 97.5% of a neutralized 80/20 tallow/coco fatty acid soap stock (EMERY® 401 Fatty Acid and EMERY® 625 Partially Hydrogenated Coconut Fatty Acid). The mixture was dried down from the neat soap moisture level of about 30% to a standard tallow/coco soap processing moisture of about 12%. This soap stock was difficult to process into a soap bar. On refining it was sticky and unsuitable for plodding and stamping. In order to process it into bars for comparative purposes it was necessary to excessively rework the stock; that is to pass it through the refining process many more times prior to plodding.

EXAMPLE 11

A tallow-free fatty acid containing a stearic acid/coco fatty acid mixture(60/40; EMERSOL® 132 Stearic Acid and EMERY® 625 Partially Hydrogenated Coconut Fatty Acid) mixture containing 5% alkyl polyglycoside (basis 100% activity; GLUCOPON® 625 surfactant) was neutralized and processed to form high moisture soap stock as described in Example 1. There were no difficulties in processing this mixture into soap bars.

EXAMPLE 12

A 50/50 (W/W) mixture of the soap stocks from Examples 9 and 11 were mixed and then processed into a soap bar according to the procedure of Example 1. There were no difficulties in processing this mixture into soap bars.

EXAMPLE 13

The soap stocks from Examples 9 and 11 were mixed and then processed into a soap bar according to the procedure of Example 1. The panel test results for the bars generated from examples 10 and 12 are given in Table 3. Example 9 is included as a performance standard.

TABLE 3

| Bars from Example # | Average Panel Rating for Flash Foaming | Average Panel Rating for Lather Volume | Average Panel Rating for Rich/Creaminess |
|---|---|---|---|
| Example 9 | 2.0 | 1.8 | 2.4 |
| Example 10 | 2.8 | 2.8 | 3.5 |
| Example 12 | 3.0 | 3.1 | 3.5 |

What is claimed is:

1. A process for making a personal cleansing bar having a high moisture content comprising the steps of: (1) forming a soap composition comprised of from about 80 to about 99% by weight of a neutralized tallow-free fatty acid mixture and from about 1 to about 20% by weight of an alkyl polyglycoside of the formula I $$R_1O(Z)_a \qquad \text{I}$$

wherein $R_1$ is a monovalent organic radical having from about 6 to about 30 carbon atoms; Z is saccharide residue having 5 or 6 carbon atoms; a is a number having a value from 1 to about 6, wherein said tallow-free fatty acid mixture has an iodine value of less than about 7 and wherein the above percentages are based on the total weight of the fatty acid mixture and the alkyl polyglycoside; (2) finishing said soap composition to produce said bar having from about 15% to about 30% by weight of water.

2. The process of claim 1 wherein said tallow-free fatty acid mixture is comprised of a first fatty acid component and a second fatty acid component.

3. The process of claim 2 wherein said first fatty acid component is coco fatty acid or palm kernel fatty acid.

4. The process of claim 3 wherein said first fatty acid component is coco fatty acid.

5. The process of claim 3 wherein said coco fatty acid is comprised of from about 45% to about 55% by weight lauric acid, from about 15% to about 23% by weight of myristic acid, from about 8% to about 11% of palmitic acid, from about 1% to about 10% by weight of stearic acid, from about 1% to about 8% by weight of oleic acid, and from about 1% to about 14% by weight of caprylic and capric acids.

6. The process of claim 2 wherein said first fatty acid component is palm kernel fatty acid.

7. The process of claim 6 wherein said palm kernel fatty acid is composed primarily of from 40% to 52% by weight lauric acid, from 14% to 18% by weight of myristic acid, from 7% to 9% of palmitic acid, from 1% to 3% by weight of stearic acid, from 3% to 5% of caprylic acid, from 3% to 7% of capric acids, from 11% to 19% by weight of oleic acid, and from 0.5% to 2% by weight of linoleic acid.

8. The process of claim 2 wherein said second fatty acid component is a stearic-palmitic acid combination.

9. The process of claim 8 wherein said stearic-palmitic acid combination is comprised of from about 45% to about 65% by weight of stearic acid and from 25% to 50% by weight of palmitic acid.

10. The process of claim 8 wherein stearic-palmitic acid combination is comprised of from 1% to 40% by weight stearic acid and from about 58% to at least about 99% by weight of palmitic acid.

11. The process of claim 2 wherein the weight ratio of said first fatty acid to said second fatty acid is from about 80/20 to about 20/80.

12. The process of claim 11 wherein the weight ratio of said first fatty acid to said second fatty acid is from about 50/50 to about 40/60.

13. The process of claim 1 wherein $R_1$ is an alkyl group having from 12 to 16 carbon atoms and wherein a is about 1.6.

14. The process of claim 1 wherein $R_1$ is an alkyl group having from 8 to 16 carbon atoms and wherein a is about 1.6.

15. The process of claim 1 wherein $R_1$ is an alkyl group having from 8 to 10 carbon atoms and wherein a is about 1.7.

16. The process of claim 1 wherein said soap composition is formed by neutralizing a mixture comprised of a tallow-free fatty acid and an alkyl polyglycoside of the formula I $$R_1O(Z)_a \qquad I$$

wherein $R_1$ is a monovalent organic radical having from about 6 to about 30 carbon atoms; Z is saccharide residue having 5 or 6 carbon atoms; a is a number having a value from 1 to about 6.

17. The process of claim 1 wherein said soap composition is formed by first neutralizing a tallow-free fatty acid and then adding an alkyl polyglycoside of the formula I $$R_1O(Z)_a \qquad I$$

wherein $R_1$ is a monovalent organic radical having from about 6 to about 30 carbon atoms; Z is saccharide residue having 5 or 6 carbon atoms; a is a number having a value from 1 to about 6.

18. A process for making a personal cleansing bar having a high moisture content comprising the steps of: (1) forming a soap composition comprised of: (a) from about 80 to about 99% by weight of a neutralized tallow-free fatty acid mixture; (b) a surfactant selected from the group consisting of an anionic, nonionic, cationic, amphoteric surfactant, and a mixture thereof; and (c) from about 1 to about 20% by weight of an alkyl polyglycoside of the formula I $$R_1O(Z)_a \qquad I$$

wherein $R_1$ is a monovalant organic radical having from about 6 to about 30 carbon atoms, Z is saccharide residue having 5 or 6 carbon atoms; a is a number having a value from 1 to about 6; wherein said tallow-free fatty acid mixture has an iodine value of less than about 7; wherein the above percentages are based on the total weight of the fatty acid mixture and the alkyl polyglycoside; and (2) finishing said soap composition to produce said bar having from about 15% to about 30% by weight of water.

19. The process of claim 18 wherein said surfactant is an alkali metal salt of an alkyl isethionate; a sarcosinate; a sulfosuccinate; a taurate; or an ethoxylated fatty alcohol.

20. The process of claim 19 wherein said alkyl isethionate is sodium cocoyl isethionate or sodium lauryl isethionate.

21. A process for making a personal cleansing bar having a high moisture content comprising the steps of: (1) forming a soap composition by mixing: (a) a first base having a moisture content of from about 15% to about 30% by weight and which is comprised of a neutralized tallow-free fatty acid mixture and an alkyl polyglycoside of the formula I $$R_1O(Z)_a \qquad I$$

wherein $R_1$ is a monovalent organic radical having from about 6 to about 30 carbon atoms; Z is saccharide residue having 5 or 6 carbon atoms; a is a number having a value from 1 to about 6, wherein said tallow-free fatty acid mixture has an iodine value of less than about 7; and, (b) a second base having a moisture content of less than about 15% and which is comprised of neutralized tallow/coco fatty acid; (2) finishing said soap composition to produce said bar having from about 15% to about 30% by weight of water; wherein the neutralized tallow-free fatty acid mixture and the neutralized tallow/coco fatty add are present in a total quantity of from about 80 to about 99% by weight, and the alkyl polyglycoslde is present in from about 1 to about 20% by weight, the above percentages being based on the total weight of neutralized tallow-free fatty acid mixture, neutralized tallow/coco fatty acid, and alkyl polyglycoside.

22. The process of claim 21 wherein said tallow-free fatty acid mixture is comprised of a first fatty acid component and a second acid component.

23. The process of claim 22 wherein said first fatty acid component is coco fatty acid or palm kernel fatty acid.

24. The process of claim 23 wherein said first fatty acid component is coco fatty acid.

25. The process of claim 23 wherein said coco fatty acid is comprised of from about 45% to about 55% by weight lauric acid, from about 15% to about 23% by weight of myristic acid, from about 8% to about 11% of palmitic acid, from about 1% to about 10% by weight of stearic acid, from about 1% to about 8% by weight of oleic acid, and from about 1% to about 14% by weight of caprylic and capric acids.

26. The process of claim 22 wherein said first fatty acid component is palm kernel fatty acid.

27. The process of claim 26 wherein said palm kernel fatty acid is composed primarily of from 40% to 52% by weight lauric acid, from 14% to 18% by weight of myristic acid, from 7% to 9% of palmitic acid, from 1% to 3% by weight of stearic acid, from 3% to 5% of caprylic acid, from 3% to 7% of capric acids, from 11% to 19% by weight of oleic acid, and from 0.5% to 2% by weight of linoleic acid.

28. The process of claim 22 wherein said second fatty acid component is a stearic-palmitic acid combination.

29. The process of claim 28 wherein stearic-palmitic acid combination is comprised of from about 45% to about 65% by weight of stearic acid and from 25% to 50% by weight of palmitic acid.

30. The process of claim 28 wherein stearic-palmitic acid combination is comprised of from 1% to 40% by weight stearic acid and from about 58% to at least about 99% by weight of palmitic acid.

31. The process of claim 22 wherein the weight ratio of said first fatty acid to said second fatty acid is from about 80/20 to about 20/80.

32. The process of claim 31 wherein the weight ratio of said first fatty acid to said second fatty acid is from about 50/50 to about 40/60.

33. The process of claim 21 wherein $R_1$ is an alkyl group having from 12 to 16 carbon atoms and wherein a is about 1.6.

34. The process of claim 21 wherein $R_1$ is an alkyl group having from 8 to 16 carbon atoms and wherein a is about 1.6.

35. The process of claim 21 wherein $R_1$ is an alkyl group having from 8 to 10 carbon atoms and wherein a is about 1.7.

36. The process of claim 21 wherein said first base is formed by neutralizing a mixture comprised of a tallow-free fatty acid and an alkyl polyglycoside of the formula I $$R_1O(Z)_a \qquad \qquad I$$

wherein $R_1$ is a monovalent organic radical having from about 6 to about 30 carbon atoms; Z is saccharide residue having 5 or 6 carbon atoms; a is a number having a value from 1 to about 6.

37. The process of claim 21 wherein said first base is formed by first neutralizing a tallow-free fatty acid and then adding an alkyl polyglycoside of the formula I $$R_1O(Z)_a \qquad \qquad I$$

wherein $R_1$ is a monovalent organic radical having from about 6 to about 30 carbon atoms; Z is saccharide residue having 5 or 6 carbon atoms; a is a number having a value from 1 to about 6.

38. A process for making a personal cleansing bar having a relatively high moisture content comprising the steps of: (1) forming a soap composition by mixing: (a) a first base comprised of a neutralized tallow-free fatty acid mixture having a moisture content of from about 15% to about 30%; a surfactant selected from the group consisting of an anionic, nonionic, cationic, amphoteric surfactant, and a mixture thereof; and an alkyl polyglycoside of the formula I $$R_1O(Z)_a \qquad \qquad I$$

wherein $R_1$ is a monovalent organic radical having from about 6 to about 30 carbon atoms; Z is saccharide residue having 5 or 6 carbon atoms; a is a number having a value from 1 to about 6, wherein said tallow-free fatty acid mixture has an iodine value of less than about 7; and, (b) a second base having a moisture content of less than about 15% and which is comprised of neutralized tallow/coco fatty acid; (2) finishing said soap composition to produce said bar having from about 15% to about 30% by weight of water; wherein the neutralized tallow-free fatty acid mixture and the neutralized tallow/coco fatty acid are present in a total quantity of from about 80 to about 99% by weight, and the alkyl polygloside is present in from about 1 to about 20% by weight, the above percentages being based on the total weight of neutralized tallow-free fatty acid mixture, neutralized tallow/coco fatty acid, and alkyl polyglycoside.

39. The process of claim 38 wherein said surfactant is an alkali metal salt of an alkyl isethionate; a sarcosinate; a sulfosuccinate; a taurate; or an ethoxylated fatty alcohol.

40. The process of claim 39 wherein said alkyl isethionate is sodium cocoyl isethionate or sodium lauryl isethionate.

* * * * *